United States Patent
Ditt et al.

(10) Patent No.: US 7,129,946 B2
(45) Date of Patent: Oct. 31, 2006

(54) COMPUTER-AIDED PRESENTATION METHOD FOR A 3D SUBJECT

(75) Inventors: Hendrik Ditt, Höchstadt (DE); Norbert Rahn, Forchheim (DE); Siegfried Wach, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 458 days.

(21) Appl. No.: 10/664,836

(22) Filed: Sep. 17, 2003

(65) Prior Publication Data

US 2004/0071326 A1    Apr. 15, 2004

(30) Foreign Application Priority Data

Sep. 17, 2002  (DE) ............................... 102 43 162

(51) Int. Cl.
*G06T 15/00*    (2006.01)

(52) U.S. Cl. ........................ 345/427; 382/128; 600/424

(58) Field of Classification Search ................ 345/419, 345/427; 382/128, 154; 600/424, 425
See application file for complete search history.

(56) References Cited

U.S. PATENT DOCUMENTS

| 6,216,030 | B1 | 4/2001 | Howard et al. | 600/427 |
| 6,364,526 | B1 | 4/2002 | Ivan et al. | 378/20 |
| 6,557,558 | B1 * | 5/2003 | Tajima et al. | 128/897 |
| 6,585,651 | B1 * | 7/2003 | Nolte et al. | 600/449 |
| 6,920,347 | B1 * | 7/2005 | Simon et al. | 600/424 |
| 6,994,703 | B1 * | 2/2006 | Wang et al. | 606/10 |
| 2003/0181809 | A1 | 9/2003 | Hall et al. | |

FOREIGN PATENT DOCUMENTS

DE    102 10 646    10/2003

* cited by examiner

*Primary Examiner*—Phu K. Nguyen
(74) *Attorney, Agent, or Firm*—Schiff Hardin LLP

(57) ABSTRACT

In the borders of a computer-aided presentation method for a 3D subject, a 2D basic image of a subject and a 2D basic presentation of a 3D volume data set of the subject are determined by a computer and momentarily output as images via an output system. The basic image and the basic presentation are thereby simultaneously output by the computer, but spatially separate from one another.

32 Claims, 3 Drawing Sheets

COMPUTER-AIDED PRESENTATION METHOD FOR A 3D SUBJECT

BACKGROUND OF THE INVENTION

The present invention concerns a computer-aided presentation method for a 3D subject. Such methods are, among other things, employed in image-aided medical procedures.

In these types of methods, a 2D basic image of the subject is continually determined by the computer and momentarily output as an image via an output system. The use of such presentation methods particularly lend themselves to this approach because the equipment required for doing this is often present in the operating room. Moreover, this equipment can be more simply operated and is more cost-effective in the acquisition than equipment for a 3D imaging such as a magnetic resonance tomograph, a computer tomograph, 3D angiography device, and the like. Moreover, the determination of a volume data set that specifies a subject is not possible in real time with the current state of the art. However, the real-time capability of the imaging is an indispensable property in connection with procedures in the body.

2D images of the subject exhibit a number of disadvantages. Using 2D images of the subject, an operator (the surgeon) always has the difficult task of mentally translating the presented 2D image contents into the real three-dimensional anatomical relationships. The situation is also often posed to the operator that a preoperative procedure planning ensues using a volume data set and 2D presentations determined from the volume data set, but these planning results can not be directly mapped to 2D images available in real time during the operation.

In navigation procedures, for the most part surgical instruments equipped with position sensors are used in clinical surroundings. The current position of these instruments can thereby be shown during the procedure in image data generated prior to the operation, as the case may be after one or more of what are called registration procedures effected during the procedure. In this procedure, the not-simple operation of the position sensors is problematic. The registration procedure is also, for the most part, very complex. A further disadvantage is that the preoperative image data determined from the volume data set of the subject does not exhibit the current actuality.

In orthopedic procedures, it is further known to present a plurality of 2D images of the subject (most in the form of projections), and thus to operate a navigation. This approach remedies the disadvantage of the lacking timeliness of the preoperative 3D volume data set, since these data are replaced by x-ray images. Admittedly, no real 3D information is available with this approach, but rather only a quasi-3D information, from which the surgeon must mentally generate a 3D scenario. Moreover, in this procedure, results of an advance procedure planning that would have been implemented previously using preoperative (real) 3D image data can not be transferred so easily to the intraoperative 2D projections.

Finally, it is even known to acquire two projections of the operation field and display them as images via the output system. These projections are acquired at different angles in order to acquire quasi-spatial information about the operation field. No real 3D image information is also generated in this approach, such that again the 3D context must be mentally created by the surgeon.

In the prior, previously undisclosed German patent application 102 10 646.0 submitted on 11 Mar. 2002 with the title "Method for image presentation of a medical instrument introduced into an examination region of a patient", (herein incorporated by reference) a computer-aided presentation method for a 3D subject is specified in which a 2D basic presentation of a 3D volume data set of the subject is determined by a computer and momentarily output as an image via an output system. Furthermore, a 2D basic image of the subject is determined by the computer, and (at least partially) superimposed on the basic presentation or, respectively, mixed with it. This procedure presents a great advance, however it is not always completely satisfactory in all aspects.

SUMMARY OF THE INVENTION

The object of the present invention is to produce a computer-aided presentation method for a 3D subject, by way of which a still easier understanding of the shown circumstances is possible for an operator (e.g., a surgeon).

The object is achieved in that a 2D basic image of the subject is determined by the computer and momentarily output as an image via an output system, and that the basic image and the basic presentation by the computer are output simultaneously but spatially separate from one another.

The present invention is thus targeted in particular at intraoperative situations in which, on the one hand, intraoperative 2D image data determined in real time is used, but in addition preoperative 3D image data exists, such that the information of the 2D image data and the information of the 3D image data can mutually complement each other. However, the invention is not limited to a homogenous presentation into one another (mixing), but rather concerns a display of images next to one another.

When not only the basic image but also the basic presentation are determined in real time by the computer, the method can be applied in particularly versatile ways. In particular, the possibility exists in this case to interactively change the basic presentation.

When the basic image is defined by a basic acquisition geometry, and the basic acquisition geometry can be changed at any time, the basic image can also be adapted at any time to possible changed requirements.

When the basic acquisition geometry should be manually shifted in a basic acquisition position by an operator to adapt the basic image, it can particularly ensue exactly and reliably when, upon achieving the basic acquisition position, the computer outputs an acoustic or optical basic confirmation to the operator, and/or the basic acquisition geometry outputs a mechanical basic confirmation to the operator.

When the basic presentation and the basic image are perspective projections, and are determined such that their projection parameters coincide, both images show the subject at the same angle of view. In the ideal case, the pictures even agree. The mental alignment of the two pictures with one another is thereby particularly simple for the operator.

A determination of the projection parameters of the basic presentation, such that the projection parameters agree with the projection parameters of the basic image, is known under the term "registration". Registration methods are, for example, specified in the previously mentioned German patent document DE 102 10 646.0. They are not, as such (in and of themselves), subject matter of the present invention.

When at least one location-dependent piece of information given by the computer in regards to the volume data set is considered by the computer at a corresponding location of the basic image, the comprehension of the presented circumstance is even simpler for the operator.

The volume data set is, as a general rule, determined in advance. For example, it can represent a vascular tree inside which a catheter is to be guided. Using the volume data set, for example, a path can be set along which the catheter is to be guided. In such a case, for example, a mixing of what is called a "road map" with the basic image is possible by using a cursor in the basic presentation to mark or to select regions, and to fully automatically transfer such markings or, respectively, selections to the basic image. If necessary, it is even possible to directly couple a cursor for the basic presentation with a cursor for the basic image.

In principle, the reverse procedure is also possible. It is thus also possible to consider by a computer at a corresponding location of the basic presentation at least one location-dependent piece of information given by the computer with regards to the subject. For example, the actual momentary location of a catheter tip can be determined and indicated in the basic presentation.

However, given the consideration of location-dependent information with regards to the subject at a corresponding location of the basic presentation, it is additionally considered that—in contrast to the imaging of the three-dimensional in two-dimensions—the imaging of the basic image in the basic projection is not normally unambiguous. Rather, each point of the basic image is imaged in a line in the volume data set. This line only reduces then back to one point of the basic projection when the basic projection and the basic image are perspective projections whose projection parameters coincide.

In particular due to this indeterminacy of the imaging of the basic image in the volume data set, it is advantageous when one 2D auxiliary image of the subject, different from the basic image of the of the subject, is determined by the computer, the auxiliary image is momentarily output by the computer as an image via the output medium, and the auxiliary image of the subject is output simultaneously with the basic image and the basic projection but spatially separate from them. The determination of the auxiliary image thereby naturally ensues in real time.

Because two 2D images are then available, two lines can be determined upon marking a specific location in each of two images in the volume data set. Similar to a cross bearing, a corresponding location can thus be determined in the volume data set, and then also unambiguously (punctiform) marked in the basic projection.

Analogous to the basic image, the auxiliary image is also determined by an auxiliary acquisition geometry. Preferably, the auxiliary acquisition geometry can also be changed at any time. In a manner analogous to the basic image, a manual proceeding in a predetermined auxiliary acquisition location can again thereby ensue via an acoustic or optical auxiliary confirmation of the computer and/or a mechanical auxiliary confirmation of the auxiliary acquisition geometry.

The basic acquisition geometry comprises a basic image main axis, the auxiliary acquisition geometry an auxiliary image main axis. The image main axes normally intersect under formation of an angle of intersection at a common intersection point. The angle of intersection is preferably determined such that it is as large as possible, due to the overall information of the subject imparted by the basic and auxiliary imaging. This is particularly the case when the auxiliary image is determined relative to the basic image such that the angle of intersection is 90°.

In the case that the angle of intersection in terms of design conditions can only be maximally as large as a critical angle that is smaller than 90°, the auxiliary image is preferably determined relative to the basic image such that the angle of intersection is the same as the critical angle.

A 2D auxiliary presentation of the volume data set, different from the basic presentation of the volume data set, is also preferably determined by the computer and momentarily output as an image via the output system. The auxiliary presentation is thereby output at the same time as the basic image and the basic presentation, but spatially separate from these, if necessary also spatially separate from the auxiliary image. An even better understanding of the displayed circumstances is thereby possible for the operator. As with the basic presentation, the auxiliary presentation is also preferably determined by the computer in real time. Because of this, it can again interactively be changed.

When the auxiliary presentation and the auxiliary image are perspective projections, and are determined such that their projection parameters coincide, a mental alignment and comparison of the auxiliary image and the auxiliary presentation is again particularly simple for the operator.

Preferably, a supplementary presentation of the volume data set, independent from both the basic presentation and the auxiliary presentation, is further determined by the computer and output as an image via the output system. The supplementary presentation is also thereby simultaneously output with the basic image, the basic presentation, and the auxiliary presentation, but spatially separate from these, if necessary, also spatially separate from the auxiliary image. The presentation method is then even more versatile. In particular, for example, the supplementary presentation can be more varied without requiring that the basic and auxiliary presentations be changed.

The supplementary presentation is also preferably determined in real time, as with the basic presentation and the auxiliary presentation. It can then likewise be interactively changed.

When the images and the presentations are respectively output via a proprietary output device, for example a monitor, the output ensues in a particularly clear manner.

As implemented above, the basic and auxiliary presentations can be perspective projections. The same is naturally also true for the supplementary presentation. However, it is also possible that the presentations—individually or together—are parallel projections or sections. The basic and auxiliary images can also be perspective projections.

When the basic image, as the case may be, also the auxiliary image, is determined by x-ray radiation or by ultrasound, the determination of the images proves to be particularly simple.

DESCRIPTION OF THE DRAWINGS

Further advantages and characteristics arise from the following specification of an exemplary embodiment in connection with the drawings.

DETAILED DESCRIPTION OF THE PREFERRED EMBODIMENTS

Figure 1:
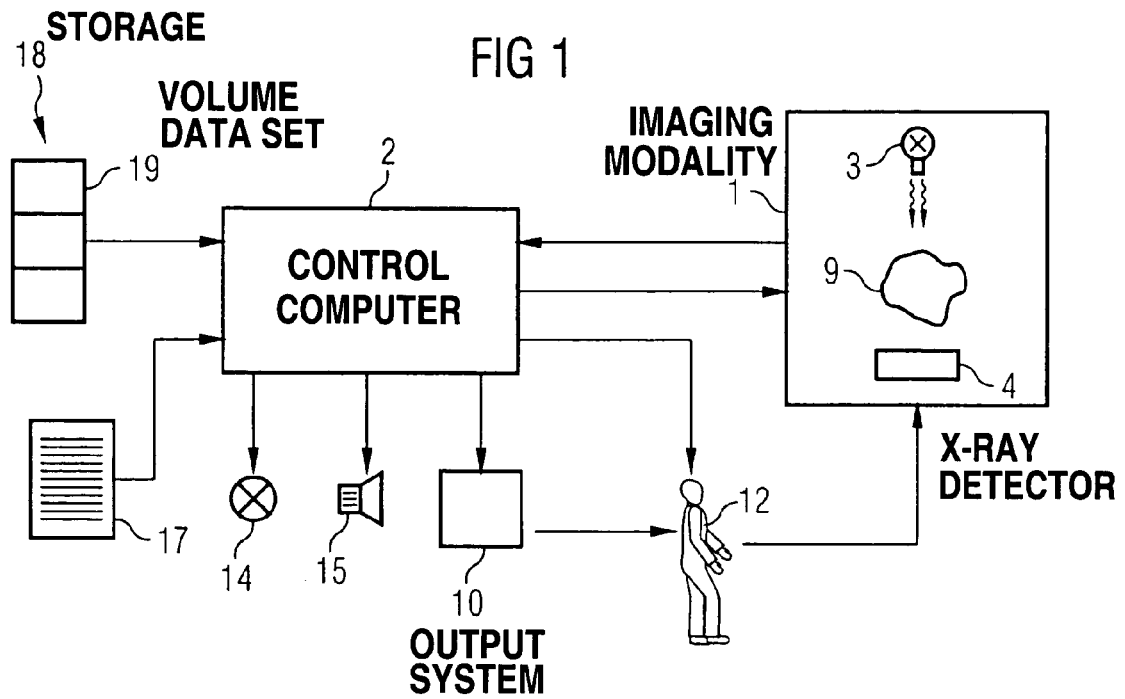
FIG. 1 is a block diagram schematic of an imaging modality.

According to an embodiment shown in FIG. 1, an imaging modality 1 is fashioned, for example, as an x-ray system 1. The x-ray system 1 is connected with a control computer 2.

Figure 2:
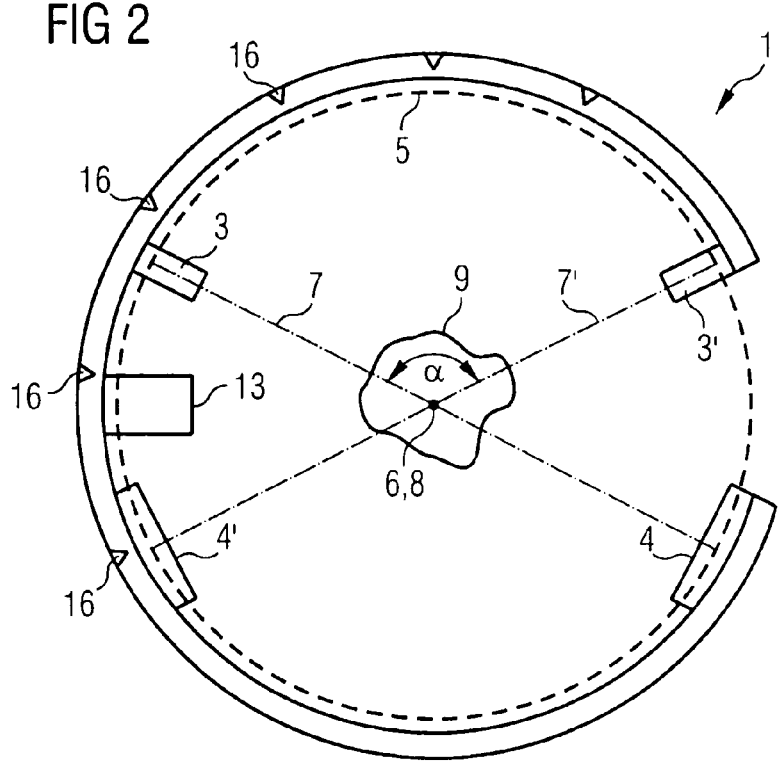
FIG. 2 is a section of the imaging modality from FIG. 1.

The x-ray system 1 may be, according to FIG. 2, fashioned as a C-arm system. It thus comprises an x-ray system that is comprised of an x-ray source 3 and an x-ray detector 4 that can be rotated on a common orbit 5 around a rotation axis 6. Each location on the orbit 5 defines an acquisition geometry. The acquisition geometry in particular comprises an imaging main axis 7 that is determined by the x-ray source 3 and the center of the x-ray detector 4. It intersects the rotation axis 6 at an intersection point 8.

A fluoroscopy image of a subject 9 detected with this acquisition geometry can thus be detected by way of the x-ray detector 4 and transmitted to the control computer 2 in real time. The corresponding image 23 of the subject 9 is then determined from this and momentarily output as an image in real time via the output system 10. In the present case of a fluoroscopy image, the image 23 is a perspective projection 23.

According to FIG. 2, in addition to the x-ray system fashioned from the x-ray source 3 and the x-ray detector 4, a further x-ray system is present that likewise comprises an x-ray source 3' and an x-ray detector 4'. The x-ray systems are thereby fashioned substantially the same. Identical components are therefore provided with the same reference numbers that are, however, provided with an apostrophe to differentiate them from the first cited x-ray system.

As is subsequently differentiated between the fluoroscopy image (projection 23) detected by the x-ray detector 4 and the fluoroscopy image (projection 23') detected by the x-ray detector 4', the former is designated as basic image 23 or, respectively, basic projection 23; the latter as auxiliary image 23' or, respectively, auxiliary projection 23'.

Figure 3:
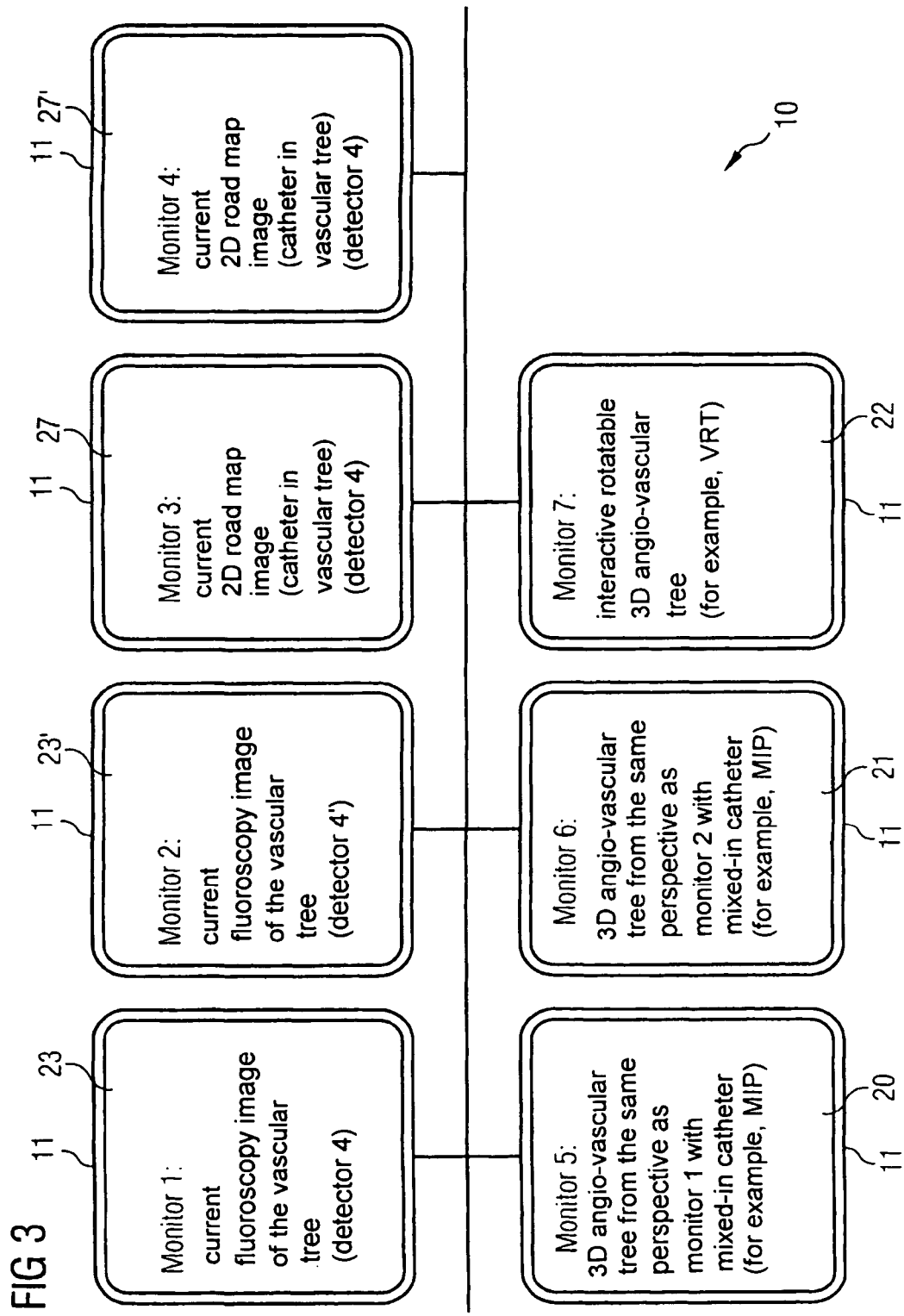
FIG. 3 is a block diagram illustrating 2D presentations of a volume data set of a subject with at least one 2D image of the subject.

According to FIG. 3, the auxiliary image 23' is likewise output by the control computer 2 via the output system 10. For this purpose, the output system 10 comprises a plurality of output devices 11, for example of monitor 11. Both projections 23, 23' are each output via their own output device 11. The output of the images 23, 23' thus namely ensues simultaneously, but separate, from one another.

The basic and auxiliary image 23, 23' are determined by the acquisition geometries, whereby, according to FIG. 2, the acquisition geometries are different from one another. In particular, the image main axes 7, 7' intersect under formation of an angle of intersection α in the intersection point 8. Thus the auxiliary image 23' is also different from the basic image 23.

The auxiliary image 23' is determined relative to the basic image 23, such that the angle of intersection α does not fall below a minimal value. The angle of intersection α should preferably be 90°. When this is not possible because a critical angle under which the image main axes 7, 7' can maximally intersect is less than 90°, the auxiliary image 23' is preferably determined relative to the main basic image 23 such that the angle of intersection α is equal to the critical angle. In practice, it has turned out that good results are already achievable when the angle of intersection α was 45°.

In principle, the basic acquisition geometry and the auxiliary acquisition geometry of the x-ray systems can be set independent of one another. For example, they can be adjusted manually by an operator 12 or by the control computer 2, as indicated in FIG. 1. However, in each case, the acquisition geometries can be changed at any time.

When the changes to the acquisition geometries ensue manually via the operator 12, the start of predetermined acquisition locations is critical. For example, the momentary positions of the x-ray systems are continually detected by way of sensors from a control device 13 and filed to the control computer 2. When, for example, the basic acquisition geometry reaches a predetermined acquisition location, the computer 2 outputs an optical confirmation to the operator 12 via a screen or a schematically indicated signal lamp 14.

Alternatively (or in addition), an acoustic confirmation can also ensue upon reaching the desired acquisition location via a small loudspeaker 15. It is also possible that the x-ray system 1 itself comprises schematically indicated mechanical feedback elements 16, such that the acquisition geometry itself outputs a mechanical confirmation to the operator 12, similar to a switch with a plurality of rotary positions.

The above embodiment, with regard to the defined start of the acquisition positions, naturally similarly applies to the basic x-ray system and the auxiliary x-ray system.

The acquisition of the fluoroscopy images of the subject 9 (projections 23, 23') and presentation of the projections (23, 23') via the output device 11 may be implemented by the control computer 2 under processing of a computer program 17 with which the control computer 2 is programmed.

A storage 18 is also allocated to the control computer 2. Among other things, a volume data set 19 of the subject 9 may be stored in the storage 18. The volume data set 19 can thereby be determined using data from all imaging 3D modalities. The volume data set 19 can thus, for example, be determined by way of computer tomography, magnetic resonance tomography, 3D angiography, 3D x-ray methods, 3D ultrasound, and other imaging 3D methods such as positron emission tomography (PET) or single photon emission computer tomography (SPECT).

Controlled by the computer program 17, the control computer 2 therefore also determines at least one presentation 20 through 22 of the volume data set 19 and presents it via one of the output devices 11 of the output system 10. The control computer 2 momentarily outputs each of the presentations 20 through 22 as an image via each their own output device 11 of the output system 10. The presentations 20 through 22 are also namely thus output by the control computer 2 simultaneously, but spatially separate from one another (and also spatially separate from the images 23, 23').

According to FIG. 3, the control computer 2 outputs three presentations 20 through 22 of the volume data set 19 via one output device 11 per each. The presentations 20 through 22 are subsequently designated as basic presentation 20, auxiliary presentation 21, and supplementary presentation 22 to differentiate them from one another.

The presentations 20 through 22 are determined in real time by the control computer 2. According to FIG. 3, in particular, the basic presentation 20 and the auxiliary presentation 21 are perspective projections 20, 21. The projection parameters of the basic projection 20 coincide with the projection parameters of the basic image 23. Likewise, the projection parameters of the auxiliary presentation 21 coincide with the projection parameters of the auxiliary image 23'. In particular, the auxiliary presentation 21 is thus different from the basic presentation 20.

The supplementary presentation 22 is independent from the basic presentation 20 and the auxiliary presentation 21. According to FIG. 3, it can, in particular, be interactively changed. For example, the volume data set 19 can be presented via the supplementary presentation 22 under changing angles of view.

According to FIG. 3, the basic presentation 20 is coupled to the basic image 23, and the auxiliary presentation 21 to the auxiliary image 23'. In particular, the basic presentation 20 and the auxiliary presentation 21 are thus necessarily perspective projections 20, 21. In the present case, a mutual coupling actually exists between basic image 23 and auxiliary image 23', such that the basic presentation 20 and the auxiliary presentation 21 are also indirectly coupled with one another. Given a change of basic or auxiliary image 23, 23', it is thus possible to directly and automatically carry along the corresponding presentation 20, 21. Thus, the basic presentation and the auxiliary presentation 20, 21 can also be indirectly interactively changed.

Moreover, it is in principle also possible to decouple the basic presentation 20 from the basic image 23, and likewise as well to decouple the auxiliary presentation 21 from the auxiliary image 23'. In this case, a direct interactive change of the basic presentation and the auxiliary presentation 20, 21 is also naturally possible. Moreover, in this case, the basic and auxiliary presentations 20, 21 need not necessarily be perspective projections. Rather, in this case they can also be parallel projections or sections.

Figure 4:
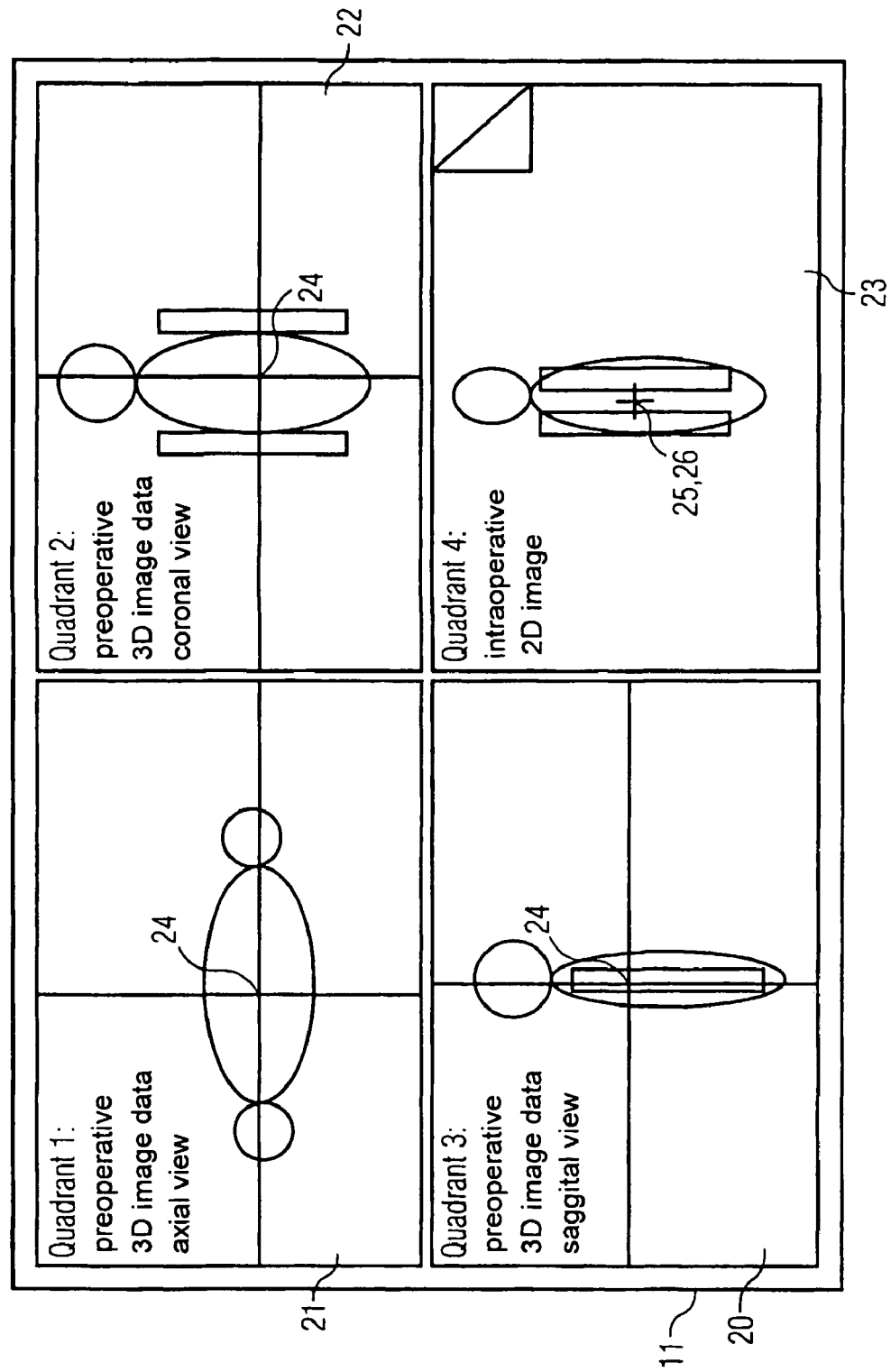
FIG. 4 is a pictorial diagram illustrating 2D presentations of a volume data set of a subject with at least one 2D image of the subject.

FIG. 4 shows an example of such a decoupling. According to FIG. 4, three presentations 20 through 22 (of the volume data set 19) and a projection 23 (of the subject) are simultaneously, but spatially separate from one another, output via the output system 10. According to FIG. 4, the three presentations 20 through 22 are three sections 20 through 22 perpendicular to one another. The projection 23 can, in individual cases, run parallel to one of the sections, but this is generally not the case.

According to FIG. 4, the sections 20 through 22 and the projection 23 are output via a single common output device 11 of the output system 10. However, they could also be respectively output via a proprietary output device 11. In any case, they are always output simultaneously but spatially separate from one another.

According to FIG. 4, it is possible that at least one location-dependent piece of information given by the control computer 2 with reference to the volume data set 19 is considered at a corresponding position of the projection 23.

For example, the three sections 20 through 22 comprise a common point 24. This point 24 corresponds to a 3D cursor 24. This 3D cursor can, for example, be mixed as a marking 25 into the projection 23. It is also possible, for example, to mix into the projection 23 a planned 3D-path for a tool that would be determined using the volume data set 19. According to FIG. 3, this ensues for example for both images 23, 23' via proprietary output devices 11 of the output system 10. In addition, to the images 23, 23', two further images 27, 27' are thus output.

It is also possible automatically to mark or to select in a similar manner a region of the volume data set 19 otherwise marked or selected in the sections 20 through 22. It is even possible to couple a cursor 26 of the projection 23 with the common point 24 of the sections 20 through 22.

The method can, in particular, also additionally be used to inspect the accuracy of the registration. For example, prominent locations of the volume data set 19 can be marked in the sections 20 through 22. By simultaneous automatic marking of the corresponding locations 25 by the control computer 2, the correctness of the registration, i.e., the imaging of the volume data set 19 in the projection 23, can then be inspected in a simple manner.

The reverse is also possible, i.e., that at least one location-dependent information given by the control computer 2 with reference to the subject 9 is considered at corresponding positions of the sections 20 through 22. This is, in particular, then possible when not only the basic image 23, but rather also the auxiliary image 23' can be used. A location in the volume data set 19 can clearly be determined then using the two projections 23, 23'. A return-to image can thus also be unambiguously implemented. Likewise, for example, a coupling of the cursor 26 with the common point 24 is thus possible, and also a marking and selection of regions in the projection 23 (or, respectively, the projections 23, 23'), whereby then the control computer 2 automatically undertakes the corresponding markings and selections in the sections 20 through 22.

The present method to mix information acquired from the projection 23 (or, respectively, the projections 23, 23') into the projections 20 through 22 can, in particular, be used to mark a surgical instrument (for example, a catheter, or, particularly, the catheter tip) in the projection 23, and then to mix this tip into the sections 20 through 22. The catheter is shown in the projections 23, 23' with, for the most part, a very high resolution, while the anatomical information of the surrounding tissue can often only be imaged roughly. Via the mixing of the catheter tip into the sections 20 through 22 (or, respectively, globally in the presentations of the volume data set 19), the catheter can therefore be considerably more precisely guided due to the present invention. The locating of the catheter tip in the projection 23 (or, respectively, in the projections 23, 23') then thereby ensues, as necessary, automatically.

According to the exemplary embodiment specified above, images 23, 23' that are projections 23, 23' are determined by x-ray radiation. This is also the most common application. However, the images 23, 23' can also be determined by another way, in particular by ultrasound, SPECT, and PET or other suitable mechanism. In these cases, the images 23, 23' are not necessarily projections 23, 23'.

The present invention has been specified in connection with a medical application. However, the invention is not limited to medical applications, but rather is universally applicable. For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

REFERENCE CHARACTERS 1 imaging modality
2 control computer
3, 3' x-ray sources
4, 4' x-ray detectors
5 cross bearing
6 axis of rotation
7, 7' image main axes
8 point of intersection
9 subject
10 output system
11 output devices
12 operator
13 control device
14 signal lamp
15 loudspeaker
16 feedback element
17 computer program
18 storage
19 volume data set
20–22 presentations
23 images
23'
24 common point
25 marking
26 cursor
27 images
27'
α angle of intersection

What is claimed is:

1. A computer-aided presentation method for a 3D subject, comprising:
   acquiring data for a 2D basic image with an acquisition device;
   determining the 2D basic image of the subject by a computer based on the acquired data for the 2D basic image;
   momentarily outputting the subject 2D basic image as an image via an output system;
   determining a 2D basic presentation of a 3D volume data set of the subject by the computer;
   momentarily outputting the 2D basic presentation of the 3D volume data set as an image via an output system, wherein the basic image and the basic presentation are output simultaneously, but spatially separate from one another by the computer; and
   determining the basic presentation and basic image as perspective projections such that their projection parameters coincide.

2. The presentation method according to claim 1, further comprising:
   determining the basic presentation in real time by the computer.

3. The presentation method according to claim 1, further comprising:
   changing the basic presentation interactively.

4. The presentation method according to claim 1, wherein:
   determining the basic image is performed utilizing a basic acquisition geometry, wherein the basic acquisition geometry is configured to be changed at any time.

5. The presentation method according to claim 4, further comprising:
   shifting the basic acquisition geometry by an operator into a basic acquisition position; and at least one of the following:
   a) producing, by the computer, an acoustic or optical basic confirmation to the operator when the basic acquisition geometry is in the basic acquisition position; and
   b) outputting a mechanical basic confirmation to the operator when the basic acquisition geometry is in the basic acquisition position.

6. The presentation method according to claim 1, further comprising:
   considering at least one piece of information related to the volume data set by the computer at a corresponding location of the basic image.

7. The presentation method according to claim 1, further comprising:
   considering at least one location-dependent piece of information related to the subject by the computer at a corresponding location of the basic presentation.

8. The presentation method according to claim 1, further comprising:
   acquiring data for a 2D auxiliary image with an acquisition device;
   determining the 2D auxiliary image of the subject that is different from the basic image of the subject by the computer, based on the acquired data for the 2D auxiliary image;
   temporarily outputting the auxiliary image by the computer as an image via the output system; and
   simultaneously outputting the auxiliary image of the subject with the basic presentation and the basic image, but spatially separate from these.

9. The presentation method according to claim 8, wherein determining the auxiliary image is performed utilizing an auxiliary acquisition geometry, wherein the auxiliary acquisition geometry is configured to be changed at any time.

10. The presentation method according to claim 9, further comprising:
    manually shifting the auxiliary acquisition geometry by an operator into an auxiliary acquisition position, and at least one of the following:
    a) producing, by the computer, acoustic or optical auxiliary confirmation to the operator when the auxiliary acquisition geometry is in the auxiliary acquisition position; and b) outputting a mechanical confirmation to the operator when the auxiliary acquisition geometry is in the auxiliary acquisition position.

11. The presentation method according to claim 8, wherein:
   determining the basic image is performed utilizing a basic acquisition geometry, wherein the basic acquisition geometry is configured to be changed at any time; and
   determining the auxiliary image is performed utilizing an auxiliary acquisition geometry, wherein the auxiliary acquisition geometry is configured to be changed at any time, the basic acquisition geometry exhibiting a basic image main axis, and the auxiliary acquisition geometry exhibiting an auxiliary image main axis, the basic image main axis and the auxiliary image main axis intersecting at a common intersection point at an angle of intersection $\alpha$.

12. The presentation method according to claim 11, further comprising:
   determining the auxiliary image relative to the basic image, such that the angle of intersection is 90°.

13. The presentation method according to claim 8, further comprising:
   determining a 2D auxiliary presentation of the volume data set that is different from the basic presentation of the volume data set by the computer,
   temporarily outputting the auxiliary presentation by the computer as an image via the output system; and
   simultaneously outputting the auxiliary presentation with the basic image and the basic presentation, but spatially separate from these.

14. The presentation method according to claim 13, wherein the auxiliary presentation is spatially separate from the auxiliary image.

15. The presentation method according to claim 13, further comprising:
   determining the auxiliary presentation in real time by the computer.

16. The presentation method according to claim 13, wherein the auxiliary presentation can be changed interactively.

17. The presentation method according to claim 13, further comprising:
   determining the auxiliary presentation and the auxiliary image as perspective projections and such that their projection parameters coincide.

18. The presentation method according to claim 13, further comprising:
   determining a 2D supplementary presentation of the volume data set independent of both the basic presentation and the auxiliary presentation by the computer;
   temporarily outputting the supplementary presentation by the computer as an image via the output system; and
   simultaneously outputting the supplementary presentation with the basic image, the basic presentation, and the auxiliary presentation, but spatially separate from these.

19. The presentation method according to claim 18, wherein supplementary presentation is spatially separate from the auxiliary image.

20. The presentation method according to claim 18, further comprising:
   determining the supplementary presentation in real time.

21. The presentation method according to claim 18, wherein the supplementary presentation can be changed interactively.

22. The presentation method according claim 8, wherein at least one of to any the basic image and the auxiliary image is determined via x-ray radiation or via ultrasound.

23. The presentation method according to claim 1, wherein the images and the presentations are respectively output each via its own output device.

24. The presentation method according to claim 23, wherein at least one output devices is a monitor of the output system.

25. The presentation method according to claim 1, wherein the presentations of the volume data set are sections or perspective projections.

26. The presentation method according to claim 1, wherein the images of the subject are perspective projections.

27. A computer program for implementation of a presentation method according to claim 1.

28. A computer programmed with a computer program according to claim 27.

29. The computer according to claim 28, that is configured as a control computer for an imaging modality.

30. An imaging modality comprising with a control computer according to claim 29.

31. The imaging modality according to claim 30, wherein the imaging modality is an x-ray system.

32. A computer-aided presentation method for a 3D subject, comprising:
   determining a 2D basic image of the subject by a computer;
   momentarily outputting the subject 2D basic image as an image via an output system;
   determining a 2D basic presentation of a 3D volume data set of the subject by the computer;
   momentarily outputting the 2D basic presentation of the 3D volume data set as an image via an output system, wherein the basic image and the basic presentation are output simultaneously, but spatially separate from one another by the computer;
   determining a 2D auxiliary image of the subject that is different from the basic image of the subject by the computer;
   temporarily outputting the auxiliary image by the computer as an image via the output system;
   simultaneously outputting the auxiliary image of the subject with the basic presentation and the basic image, but spatially separate from these;
   determining the basic image is performed utilizing a basic acquisition geometry, wherein the basic acquisition geometry is configured to be chanced at any time;
   determining the auxiliary image is performed utilizing an auxiliary acquisition geometry, wherein the auxiliary acquisition geometry is configured to be changed at any time, the basic acquisition geometry exhibiting a basic image main axis, and the auxiliary acquisition geometry exhibiting an auxiliary image main axis, the basic image main axis and the auxiliary image main axis intersecting at a common intersection point at an angle of intersection $\alpha$:
   maximizing the angle of intersection $\alpha$ in terms of design conditions so that it is as large as a critical angle that is smaller than 90°, and
   determining the auxiliary image relative to the basic image such that the angle of intersection $\alpha$ is the same as the critical angle.

* * * * *